US00PP34476P2

(12) United States Plant Patent
Ammerlaan

(10) Patent No.: US PP34,476 P2
(45) Date of Patent: Aug. 2, 2022

(54) ***ECHEVERIA* PLANT NAMED 'OVPEARLS10'**

(50) Latin Name: ***Echeveria elegans* x *pulidonis***
Varietal Denomination: OVPEARLS10

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/803,283

(22) Filed: Apr. 19, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

A new and distinct variety of *Echeveria* plant named 'OVPEARLS10' which is characterized by a flattened globular profile with foliage arranged in a compact basal rosette, moderately to strongly glaucous foliage that is covered with a layer of greyed-green epicuticular wax which gives the foliage a pale blue-grey appearance, juvenile foliage with a greyed-red laminar tip, and mature foliage with a purple to greyed-purple apical margins and laminar tip. The new variety has shown to be uniform and stable in the resulting generations from asexual propagation.

4 Drawing Sheets

Latin name of the genus and species: The Latin name of the genus and species of the novel variety disclosed herein is *Echeveria elegans* x *pulidonis*.

Variety denomination: The inventive variety of *Echeveria* disclosed herein has been given the variety denomination 'OVPEARLS10'.

BACKGROUND OF THE INVENTION

Parentage: 'OVPEARLS10' is a seedling selection, presumed to be the result of the open-pollination of an unnamed *Echeveria elegans* plant (unpatented), the seed parent, and a plurality of unnamed *Echeveria pulidonis* plants (not patented), the presumed pollen parent. The exact pollen parent is unknown. The crossing is believed to have occurred in the summer of 2016 at a commercial greenhouse in Bleiswijk, the Netherlands. In early 2017, one seedling from said cross was observed to exhibit unique foliage and growth characteristics when compared to the parent plants and all other progeny. After confirming the stability of the unique characteristics first observed, the new plant was selected for commercialization and given the name, 'OVPEARLS10'

Asexual Reproduction: Asexual reproduction of the new cultivar 'OVPEARLS10', by way of rooting leaf cuttings, was first initiated in the autumn of 2017 at the inventor's commercial greenhouse in Bleiswijk, the Netherlands. Through eleven subsequent generations, the unique features of this cultivar have proven to be stable and true to type.

SUMMARY OF THE INVENTION

The cultivar 'OVPEARLS10' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS10'. These characteristics in combination distinguish 'OVPEARLS10' as a new and distinct *Echeveria* cultivar:

1. 'OVPEARLS10' exhibits an abundance of succulent foliage with a concave and upwardly curved aspect, arranged in a compact rosette; and
2. 'OVPEARLS10' exhibits near-oblong to broad oblanceolate foliage with an abruptly acute apex and a mucronate tip, occasionally with light undulation on one side of the lamina; and
3. 'OVPEARLS10' exhibits moderately to strongly glaucous foliage that is covered with a layer of greyed-green epicuticular wax which gives the foliage a pale blue-grey general coloration; and
4. 'OVPEARLS10' exhibits juvenile foliage with a greyed-red laminar tip; and
5. 'OVPEARLS10' exhibits mature foliage with apical margins and laminar tips that are purple to greyed-purple.

BOTANICAL DESCRIPTION OF THE PLANT

Figure 1:
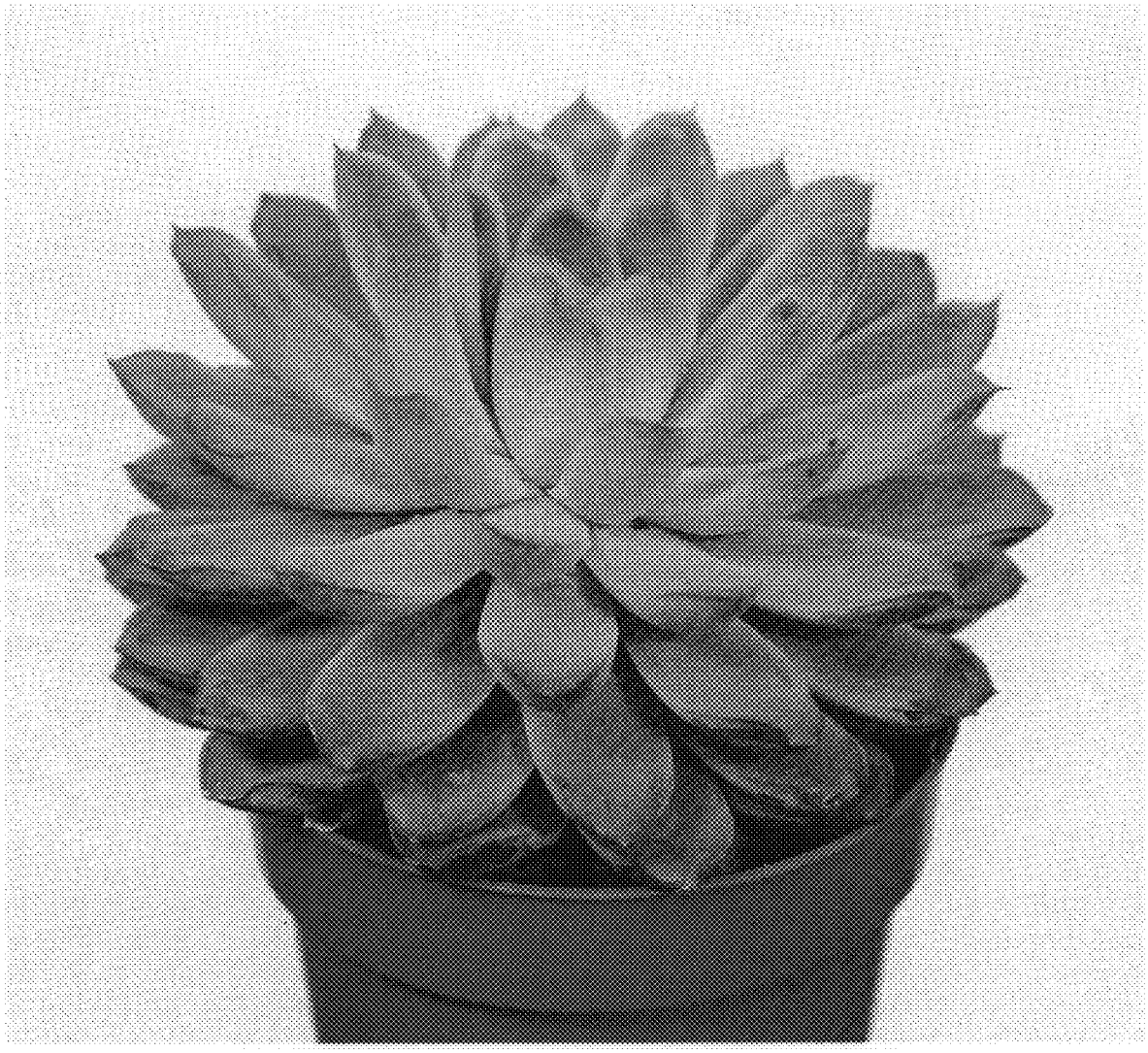
FIG. 1 illustrates, as nearly true as it is reasonably possible to make the same in color photographs of this type, an exemplary plant of 'OVPEARLS10' grown in a commercial greenhouse in Bleiswijk, the Netherlands. This plant is approximately 1 year old, shown planted in an 8.5 cm container.
Figure 2:
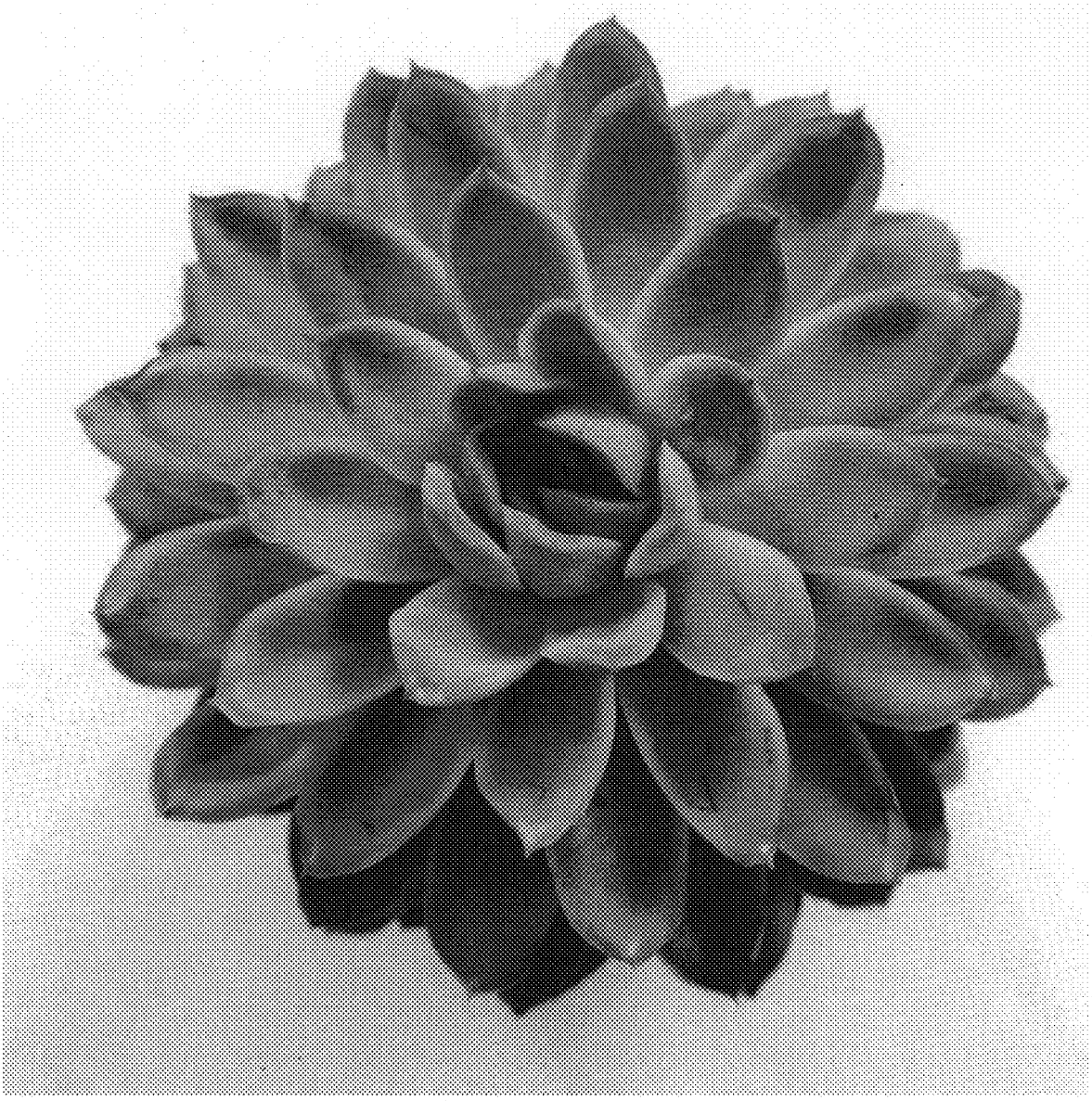
FIG. 2 illustrates, as nearly true as it is reasonably possible to make the same in color photographs of this type, the typical foliage arrangement of 'OVPEARLS10'.
Figure 3:
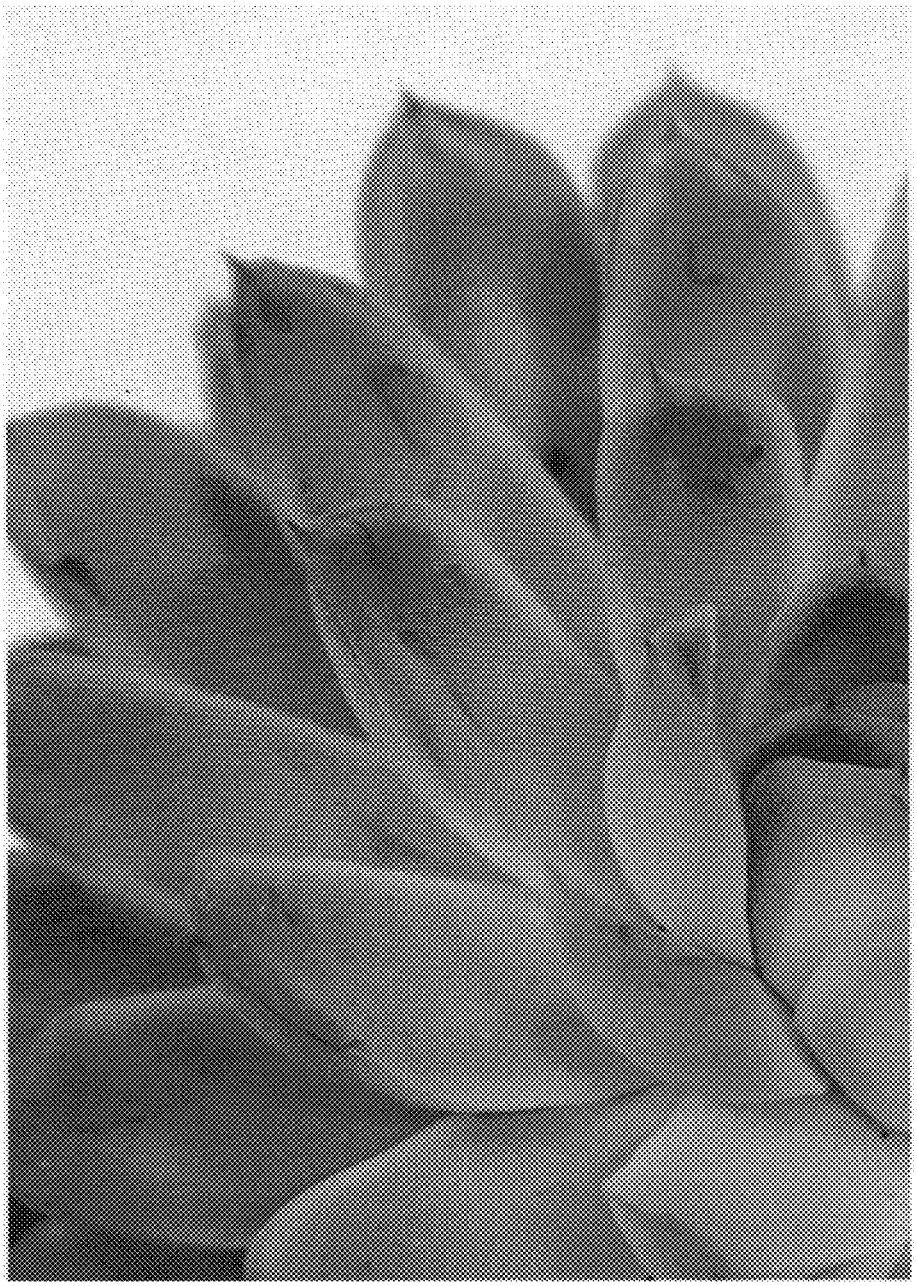
FIG. 3 illustrates, as nearly true as it is reasonably possible to make the same in color photographs of this type, the adaxial surface of the mature foliage 'OVPEARLS10'.
Figure 4:
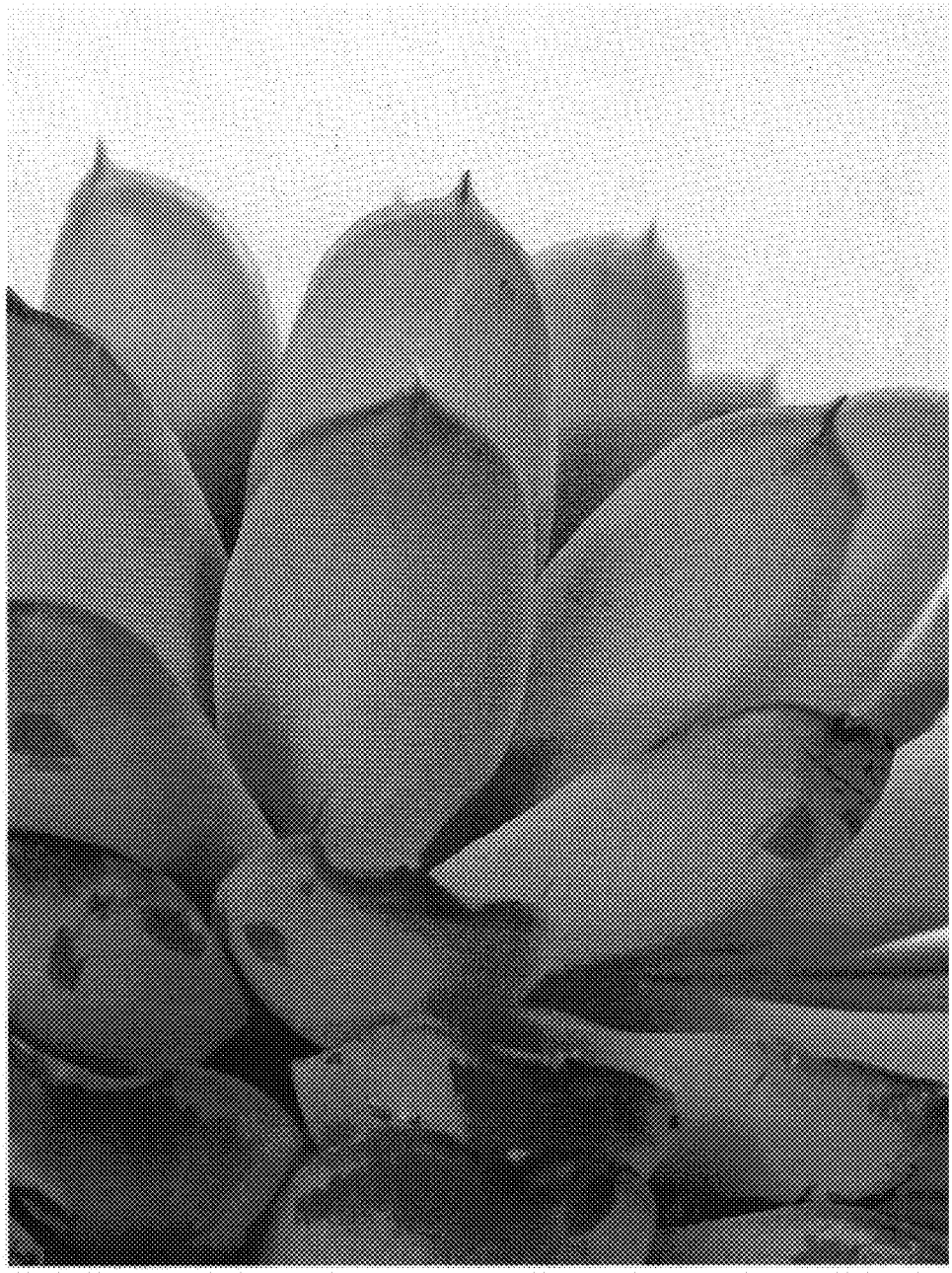
FIG. 4 illustrates, as nearly true as it is reasonably possible to make the same in color photographs of this type, the abaxial surface of the mature foliage 'OVPEARLS10'.

The following observations and measurements made in December of 2021 describe averages from a sample set of six specimens of 1 year old 'OVPEARLS10' plants grown in 8.5 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS10' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS10' and a comparison with the parent plants and closest known comparator is provided below.

Plant description:

*Growth habit*.—Succulent perennial with foliage growing in a compact, non-branched basal rosette, eventually forms a short stem with age.

*Plant form*.—Flattened globular.

*Height from soil level to top of foliar plane*.—7.5 cm.

*Plant spread*.—Average of 10.9 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Main stem dimensions*.—2.4 cm long and 0.3 cm in diameter.

*Internode length*.—0.3 cm.

*Aspect*.—Rounded.

*Attitude*.—Nearly vertical.

*Strength*.—Moderately strong.

*Texture and luster*.—Glabrous, glaucous; covered with a thin layer of epicuticular wax which is colored a translucent greyed-green, nearest to RHS 192C.

*Color, when developing*.—Greyed-green, nearest to RHS 192C.

*Color of mature stem*.—Greyed-green, nearest to RHS 192B.

*Color at internodes*.—Greyed-green, nearest to RHS 192B.

Foliage:

*Arrangement*.—Rosette.

*Division*.—Simple.

*Attachment*.—Sessile.

*Quantity*.—Approximately 90 leaves per rosette.

*Shape*.—Near-oblong to broad oblanceolate.

*Dimensions*.—4.2 cm long, 1.6 cm wide, and 0.7 cm thick, on average.

*Aspect*.—Concave; distalmost portion of the lamina is curled upward at an average angle of 30 degrees.

*Attitude*.—Juvenile foliage at the center of the rosette exhibits a near-vertical attitude; foliage becomes progressively more relaxed as it matures and becomes nearly horizontal to slightly pendulous at the outer whorls of the rosette.

*Apex*.—Abruptly acute with a mucronate tip; occasionally with light undulation on one side of the lamina.

*Base*.—Long cuneate.

*Margin*.—Entire; occasionally with some slight undulation along one side of the lamina, at and near the apex.

*Pubescence, texture and luster of the adaxial surface*.—Glabrous, smooth, and matte; moderately to strongly glaucous.

*Pubescence, texture and luster of the abaxial surface*.—Glabrous, smooth, and matte; moderately to strongly glaucous.

*Color*.—Juvenile foliage, adaxial surface — Yellow-green, nearest to RHS 147B; fading lighter towards the base, nearest to RHS 147D; margined with a lighter shade of yellow-green, nearest to RHS 148D; laminar tips are lightly suffused with greyed-red, nearest to RHS 181A. Leaves are covered with a thin layer of epicuticular wax which is colored greyed-green, nearest to RHS 189B. Juvenile foliage, abaxial surface — Greyed-green, nearest to a mixture of RHS 191A and 191B; fading lighter towards the base, nearest to a mixture of RHS 193A and 193B; margined yellow-green, nearest to RHS 147D; laminar tips are lightly suffused with greyed-red, nearest to RHS 181A. Leaves are covered with a thin layer of epicuticular wax which is colored greyed-green, nearest to a mixture of RHS 188A and 188B. Mature foliage, adaxial surface — Green, nearest to RHS NN137C; fading lighter to yellow-green towards the base, nearest to RHS 146D; margins are yellow-green, nearest to RHS 147D, and suffused with purple, distally, nearest to RHS N77B; laminar tip is slightly darker, nearest to a mixture of RHS N77A and N77B. Leaves are covered with a thin layer of epicuticular wax which is colored greyed-green, nearest to RHS 189B. Mature foliage, abaxial surface — Nearest to a mixture of green and yellow-green, RHS 138B and 147C; fading lighter towards the base, nearest to RHS 147C; apex, apical margins, and laminar tip are moderately suffused with greyed-purple, nearest to a mixture of RHS 189A and 189B. Leaves are covered with a thin layer of epicuticular wax which is colored greyed- green, nearest to a mixture of RHS 188A and 188B.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS10' differ from the seed parent, an unnamed *Echeveria elegans* plant (not patented) in the following characteristics described in Table 1 below.

TABLE 1

| Characteristic | 'OVPEARLS10' | The seed parent. |
|---|---|---|
| Foliage width. | Narrower than the seed parent. | Wider than 'OVPEARLS10'. |
| Foliage aspect. | Less concaved than the seed parent. | More concaved than 'OVPEARLS10'. |
| Undulation of the foliar margins. | Lightly undulated. | No undulation. |
| Coloration of the juvenile laminar tip. | Greyed-red. | Yellow-green. |

Plants of the new cultivar 'OVPEARLS10' differ from the pollen parent, an unnamed *Echeveria pulidonis* plant (not patented) in the following characteristics described in Table 2 below.

TABLE 2

| Characteristic | 'OVPEARLS10' | The pollen parent. |
|---|---|---|
| Plant profile. | Flattened globular, yet nearer to globular by comparison with the parent. | Flattened globular, yet nearer to flattened by comparison with 'OVPEARLS10'. |
| Foliage length. | Shorter than the parent. | Longer than 'OVPEARLS10'. |

TABLE 2-continued

| Characteristic | 'OVPEARLS10' | The pollen parent. |
|---|---|---|
| Foliage width. | Narrower than the parent. | Broader than 'OVPEARLS10'. |
| Foliage thickness. | Thicker than the parent. | Thinner than 'OVPEARLS10'. |
| Coloration of the juvenile foliar margins and laminar tip. | Yellow-green with a greyed-red laminar tip. | Apical margins and laminar tip are colored greyed-red. |

COMPARISONS WITH THE CLOSEST KNOWN COMPARATOR

Plants of the new cultivar 'OVPEARLS10' differ from *Echeveria* hybrid 'OVPEARLS11' (U.S. Plant patent application Ser. No. 17/803,281 filed concurrently), which is the closest known comparator, in the following characteristics described in Table 3 below.

TABLE 3

| Characteristic | 'OVPEARLS10' | 'OVPEARLS11' |
|---|---|---|
| Plant size. | Taller but less spreading, relative to 'OVPEARL11'. | Shorter with a greater spread, relative to 'OVPEARLS10'. |
| Foliage size. | Smaller than 'OVPEARLS11'. | Larger than 'OVPEARLS10'. |
| Foliage shape. | Near-oblong to broad oblanceolate. | Oblanceolate. |
| Foliar margin undulation. | Occasionally with some slight undulation along one side of the lamina, at and near the apex. | Entire. |
| Coloration of the mature foliar margins and laminar tip. | Apical margins and laminar tip are more prominently colored purple to greyed-purple. | Distal margins and laminar tip are conspicuously margined purple to greyed-purple. |

That which is claimed is:

1. A new and distinct variety of *Echeveria elegans* x *pulidonis* plant named 'OVPEARLS10', substantially as described and illustrated herein.

* * * * *